United States Patent

Shave

[11] Patent Number: 5,358,498
[45] Date of Patent: Oct. 25, 1994

[54] NEEDLED SUTURE

[75] Inventor: William H. Shave, New York, N.Y.

[73] Assignee: Deknatel Technology Corporation, Inc., Fall River, Mass.

[21] Appl. No.: 474,594

[22] Filed: Feb. 1, 1990

[51] Int. Cl.⁵ .......................................... A61B 17/00
[52] U.S. Cl. .................................. 606/224; 606/225
[58] Field of Search ........................... 606/222–228, 606/230; 285/381

[56] References Cited

U.S. PATENT DOCUMENTS

| | | | |
|---|---|---|---|
| 1,613,206 | 3/1922 | Souttar | 606/226 |
| 2,240,330 | 7/1938 | Flagg et al. | 606/226 |
| 2,577,466 | 12/1951 | Jones | 154/118 |
| 2,712,196 | 7/1955 | Allen | 43/43.1 |
| 2,928,395 | 3/1960 | Forbes et al. | 128/335.5 |
| 3,311,110 | 3/1967 | Singerman et al. | 128/335.5 |
| 3,579,805 | 5/1971 | Kast | 29/447 |
| 3,611,551 | 10/1971 | Shave et al. | 128/339 |
| 3,698,853 | 10/1972 | Wilson | 606/229 |
| 3,799,169 | 3/1974 | Beroff et al. | 128/339 |
| 3,875,946 | 4/1975 | Duncan | 128/339 |
| 3,890,975 | 6/1975 | McGregor | 128/339 |
| 3,896,814 | 7/1975 | Vivien et al. | 606/229 |
| 3,918,455 | 11/1975 | Coplan | 128/339 |
| 3,924,630 | 12/1975 | Walldorf | 128/339 |
| 3,926,194 | 12/1975 | Greenberg et al. | 128/339 |
| 3,943,933 | 3/1976 | Gertzman | 128/339 |
| 3,963,031 | 6/1976 | Hunter | 606/227 |
| 3,981,307 | 9/1976 | Borysko | 128/339 |
| 4,010,756 | 3/1977 | Dumont et al. | 128/404 |
| 4,054,144 | 10/1977 | Hoffman et al. | 128/339 |
| 4,127,133 | 11/1978 | Martinez | 606/227 |
| 4,169,447 | 10/1979 | Bokros | 604/175 |
| 4,359,053 | 11/1982 | Benjamin | 128/339 |
| 4,411,055 | 10/1983 | Simpson et al. | 29/447 |
| 4,433,688 | 2/1984 | Bichon | 606/229 |
| 4,470,415 | 9/1984 | Wozniak | 128/334 R |
| 4,549,752 | 10/1985 | Nimhe et al. | 285/381 |
| 4,596,728 | 6/1986 | Yang et al. | 428/36 |
| 4,630,617 | 12/1986 | Ritter et al. | |
| 4,660,559 | 4/1987 | McGregor et al. | 128/339 |
| 4,672,734 | 6/1987 | Kawada et al. | 29/517 |
| 4,722,384 | 2/1988 | Matsutani | 163/1 |
| 4,799,311 | 1/1989 | Matsutani | 29/209 |
| 4,805,292 | 2/1989 | Noguchi | 29/445 |
| 4,832,025 | 5/1989 | Coates | 128/335.5 |
| 4,922,904 | 5/1990 | Uetake et al. | 606/226 |
| 4,926,860 | 5/1990 | Stice et al. | 606/224 |
| 4,932,963 | 6/1990 | Ritter et al. | 606/224 |
| 5,007,922 | 4/1991 | Chen et al. | 606/228 |
| 5,035,707 | 7/1991 | Korthoff | 606/227 |
| 5,041,128 | 8/1991 | Korthoff | 606/224 |

FOREIGN PATENT DOCUMENTS 2520224  8/1983  France ................. A61B 17/06

OTHER PUBLICATIONS

Raychem Corporation, "Thermofit ®Kynar Tubing" Mar. 6, 1984, p. 6t.

Primary Examiner—Stephen C. Pellegrino
Assistant Examiner—Gary Jackson
Attorney, Agent, or Firm—Pennie & Edmonds

[57] ABSTRACT

A needle-suture combination employing a heat shrunk sleeve to attach a needle to a suture. One or more heat shrunk sleeves might also be incorporated into the combination to provide a controlled release suture or to provide a linked tandem suture.

8 Claims, 3 Drawing Sheets

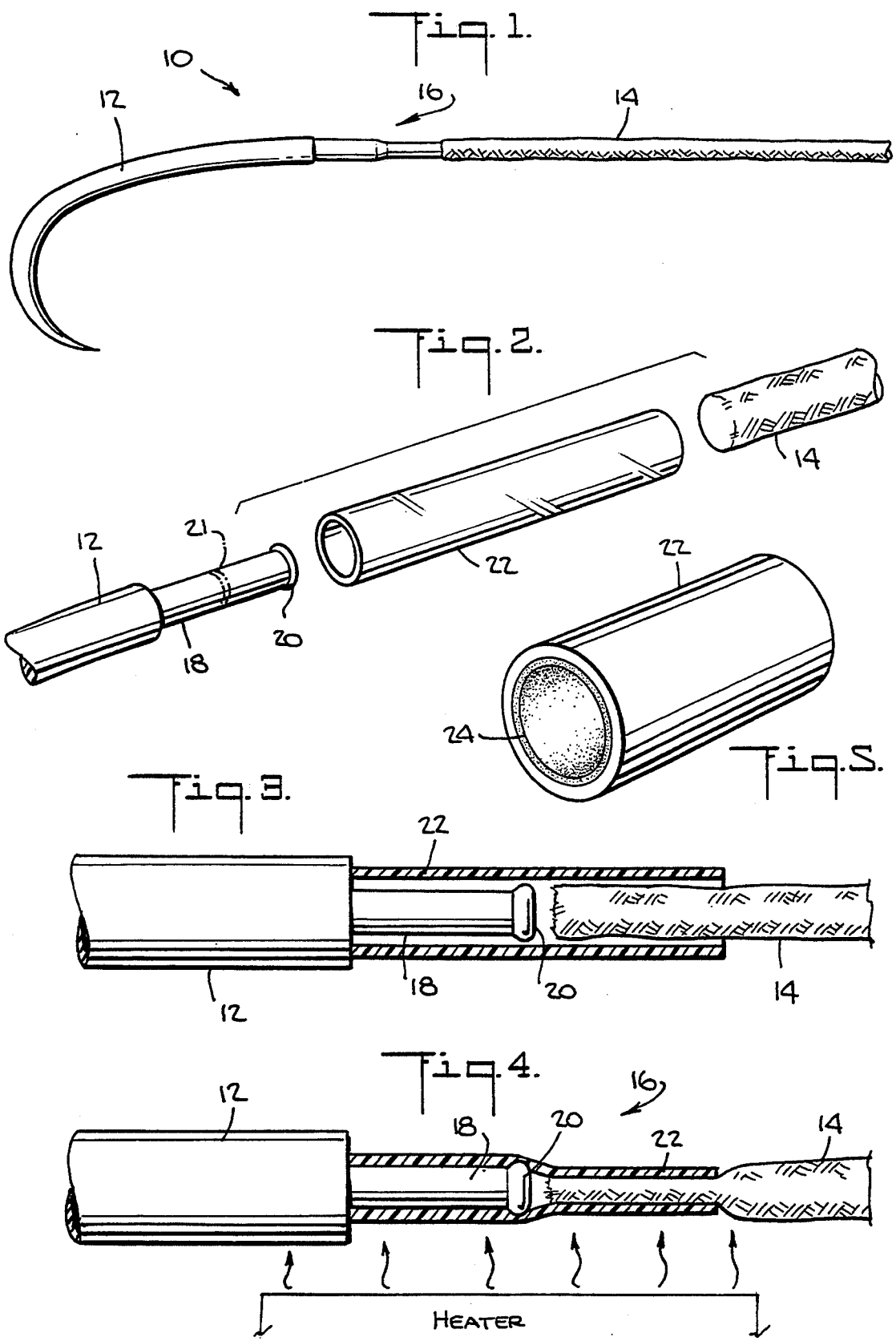

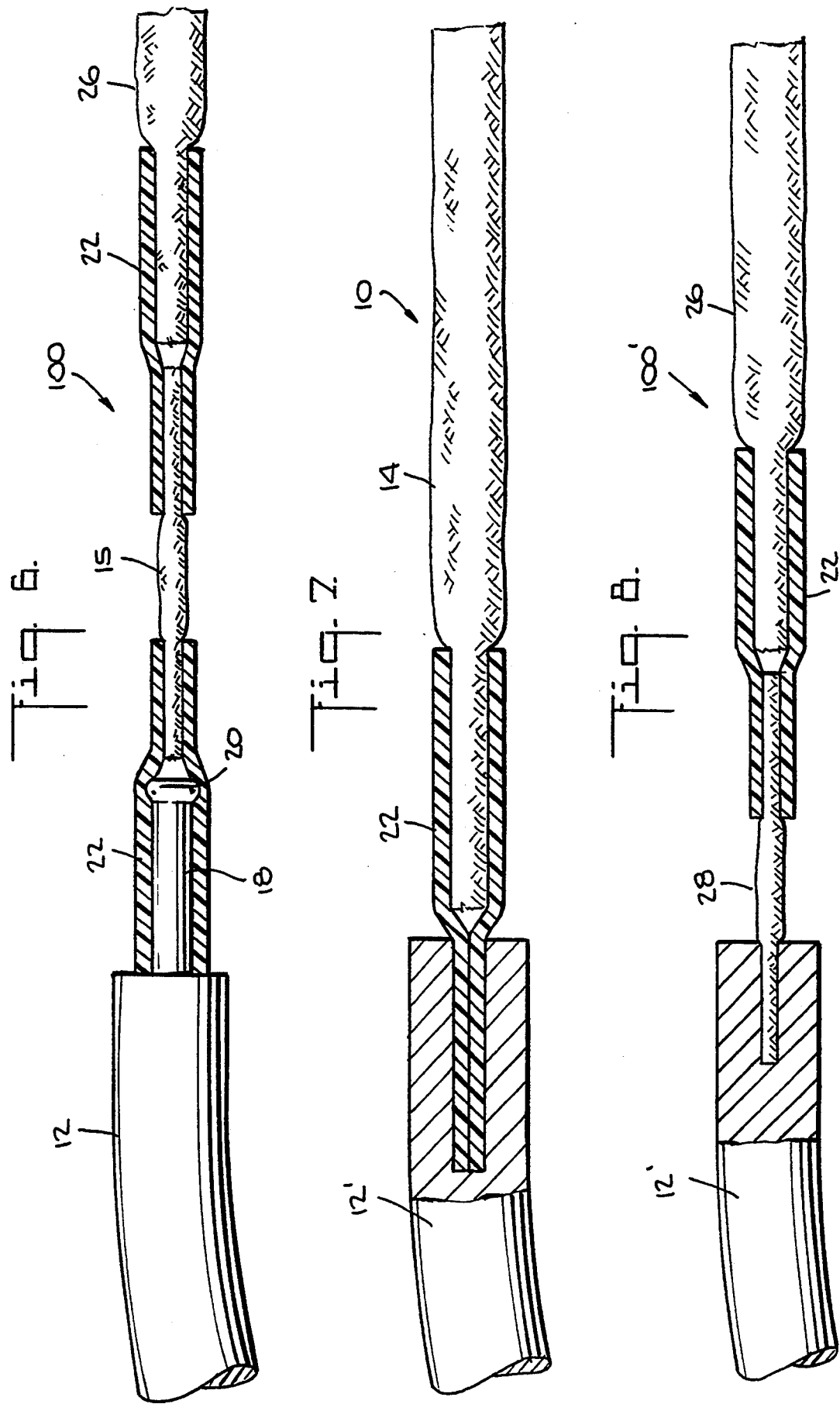

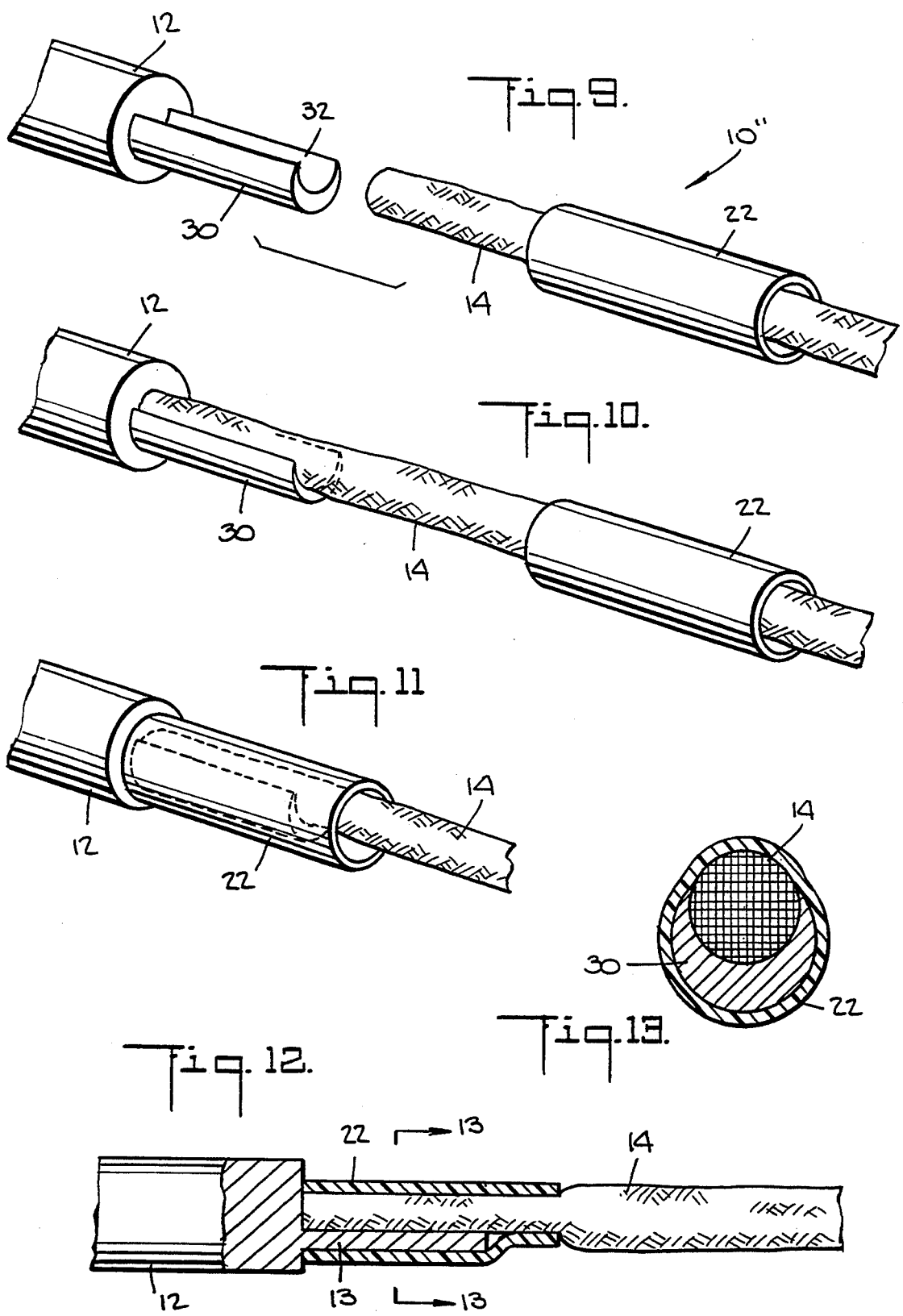

NEEDLED SUTURE

BACKGROUND OF THE INVENTION

The present invention pertains generally to needled sutures. More particularly, the invention relates to the utilization of a shrink sleeve heat shrunk-fit to couple together a needle and a suture. A shrink sleeve or shrink sleeves might additionally be utilized to couple a needle and a number of sutures for providing a linked tandem suture or a controlled release suture or for linking a number of sutures.

There exist in the art a variety of teachings pertaining to the attachment of a suture to a suture needle. Exemplary of needle suture connection might be the placement of an end of a suture into a hole or channel in the blunt end of a needle whereinafter the hole or channel is mechanically swaged or crimped onto the suture so that the suture is firmly held within the needle. Another teaching for anchoring a suture to a needle might be the placement of a suture tip into a recess in the blunt end of a needle whereafter the needle is heated to expand the suture tip within the recess into tight engagement with the recess walls. Yet another teaching for connecting a needle and a suture might be by means of a needle shank portion of smaller diameter than the needle diameter, with the shank being inserted into an internal or central bore provided in the suture for tight fitting engagement and anchoring therein. Still another teaching to effect a needle-suture connection might be the use of the techniques of heating, soldering, brazing or gluing a hollow metal tubular suture for coupling the tubing to a surgical needle. Another teaching might be the use of an eyeless surgical needle in the butt end of which is an opening wherein a flexible suture leader is crimped and a connector sleeve of high strength metal is crimped to capture a surgical suture.

Suture needles are formed from a relatively soft metal wire-like material. A segment of wire of sufficient length for both the needle and a handle (for holding the needle during the manufacture thereof) is cut from the main wire source. The length is then straightened, formed with a point at the front end, and a part of the shank to the rear of the point may be flattened to provide a place for the surgeon to grip the needle.

When using the channel method for attaching the suture to the needle, a channel is formed in the needle, rearward of the shank while the needle is still in its initial, relatively soft condition. This groove is stamped into the needle by means of a V-shaped die. The V-shape of the die is necessary to assure that a sufficient force is concentrated at the appropriate place on the channel to form a groove of a sufficient depth without damaging the walls of the newly formed channel.

The needle shaft is now bent to the desired curvature and the needle is hardened. This may be accomplished by placing the needles into a vacuum furnace at approximately 980° C. to 1040° C. followed by tempering at about 260° C. to take out the brittleness. The finished needle may have a Rockwell hardness of approximately 49 to 55.

Since the suture could not withstand the heat treatments, it must of course be attached to the needle after hardening. However, it is impossible to bend the hardened channel walls to close them onto a suture without cracking or twisting the walls. Thus, before closing the channel walls onto suture it is necessary to soften the channel walls by annealing. Of course, care must be taken to prevent the softening effect of the annealing procedure from being felt forward of the channel walls along the shank or the needle point.

Following annealing the needle is electroplated, and the handle part is chopped off leaving the channel open to the rear. The suture is then inserted and the channel walls are closed onto the suture, preferably by crimping to hold the suture.

Notwithstanding the necessity of the annealing procedure, it has been found that annealing has several detrimental effects. First, there is an inevitable drift of heat down the shank of the needle causing some undesirable annealing effect on the shank of the needle itself. In addition, the annealing process invariably decreases the "stainlessness" of the needle, that is the ability of the needle to resist rust, especially at the softened channel.

Further, the "chop off" of the handle from the main part of the needle is less clean with a softer annealed needle than with a harder needle. This "chop off" is accomplished through that portion of the needle which has the channel formed into it. The harder the material of the channel, the cleaner the chop off, and the smaller the resultant burr. The annealing process, by softening the channel, prevents a clean chop off and makes it more likely for burrs to occur.

Moreover, the above disadvantages can become even more significant when the needle is treated to obtain a very high Rockwell hardness. In this case it may be necessary to anneal the needle several times, thereby significantly increasing the above noted undesirable effects.

Indeed, with a very hard needle, it is frequently impossible or difficult to accomplish the necessary softness for bending the needle material without cracking or twisting the same regardless of the number of annealing steps.

Thus, there exists a need for improvements which will permit the use of a superior means for attaching a suture to a needle while eliminating or substantially reducing the detrimental effects of annealing.

Accordingly, herein disclosed is the coupling of a needle to a suture and a suture to a suture by means of a heat shrinkable sleeve which has numerous advantages over known couplings. Specifically, attachment time is significantly less, handling and equipment costs are reduced, needle quality is improved, needle to suture and suture to suture attachment is enhanced, and a more economical needle to suture and suture to suture coupling means is presented.

SUMMARY OF THE INVENTION

The present invention is directed toward a needle-suture combination comprising a needle having first and second ends, a suture, and a heat shrunk sleeve surrounding and securing therewithin a first end of the needle and an end of the suture. One of the ends of the needle might include a hub and the suture might be positioned substantially coaxially with and have an end disposed face to face with the hub in proximate or contiguous relationship. Also contemplated is the placement of the end portion of the suture in juxtaposed relationship with at least a portion of the hub and the sleeve securing therewithin at least a portion of the juxtaposed suture and hub. The hub might include one or more grooves or flanges peripherally disposed about the hub length. The suture could be positioned in a hub groove before sleeve placement. The end portion of the suture might be stiffened by means of a coating of nylon or polyester. The sleeve might further include an adhesive disposed internally along at least a portion of the length surrounded by the sleeve.

The invention additionally embodies a needle-suture combination comprising a needle having first and second ends, a first suture, a first heat shrunk sleeve surrounding and securing therewithin a first end of the needle and a first end of the first suture, and a second heat shrunk sleeve surrounding and securing therewithin a second end of the first suture and a first end of a second suture. An adhesive means might further be disposed internally along at least a portion of the length surrounded by at least one of the first and second sleeves.

In another form of the invention, the combination might comprise a needle having first and second ends with one of the ends having a recess, a suture, and a heat shrunk sleeve at a first end surrounding and securing therewithin an end of the suture with the sleeve at a second end being located and secured within the recess. The sleeve might further include an adhesive disposed internally along at least a portion of the length of the first end of the sleeve surrounding the end of the suture.

Further embodied within the invention is a needle-suture combination comprising a needle having first and second ends, a first suture, and linking means for coupling a first end of the first suture with a first end of the needle, the linking means being capable of separating the needle from the first suture by application of a predetermined axial force along the linking means, with the force being substantially less than the force necessary to break the first suture. The linking means might comprise a second suture, a first heat shrunk sleeve surrounding and securing therewithin a first end of the needle and a first end of the second suture, and a second heat shrunk sleeve surrounding and securing therewithin a second end of the second suture and the first end of the first suture. Alternatively, the linking means might comprise a second suture having a first end located and secured within a recess in a first end of the needle, and a heat shrunk sleeve surrounding and securing therewithin a second end of the second suture and a first end of the first suture.

Also embodied within the invention is a suture-suture combination. The combination might comprise a first suture having opposing end portions, a second suture having opposing end portions, and a heat shrunk sleeve surrounding and securing therewithin a first end portion of the first suture and a first end portion of the second suture.

BRIEF DESCRIPTION OF THE DRAWINGS

FIG. 1 is a schematic view of the present invention depicting a needle-suture combination embodying a heat shrunk sleeve coupling a needle and a suture.

FIG. 2 is an enlarged, partial, perspective view, in exploded form, of the component parts of the combination illustrated in FIG. 1 but prior to assemblage.

FIG. 3 is an enlarged, schematic view of the components of FIG. 2 positioned for assemblage and showing the sleeve, in section, prior to heat shrinking.

FIG. 4 is a view like that illustrated in FIG. 3 but now showing the application of heat to the sleeve to shrink fit the sleeve to provide the coupled needle and suture of FIG. 1.

FIG. 5 is an enlarged, perspective view of the sleeve prior to heat shrinking and further including a layer of adhesive located therewithin.

FIG. 6 is a partial, schematic view of a linked, tandem needle-suture combination showing two heat shrunk sleeves, in section, coupling a needle and two sutures.

FIG. 7 is a partial, schematic view of a coupled needle and suture embodying a heat shrunk sleeve, with the sleeve shown in section and a portion of the needle shown cut away to illustrate the sleeve end located in a needle recess.

FIG. 8 is a view much like that of FIG. 7 but showing a first suture located in a needle recess and a heat shrunk sleeve coupling the first suture to a second suture.

FIG. 9 is an alternate embodiment much like that of FIG. 2 but further illustrating a groove at the needle end location.

FIG. 10 is a view like that of FIG. 9 but now depicting the suture positioned in the groove at the needle end.

FIG. 11 is a view of the components of FIGS. 9 and 10 positioned for assemblage but prior to heat shrinking the sleeve.

FIG. 12 is a schematic view of the components of FIG. 11, showing the needle end in partial section and tile sleeve in full section, with the sleeve shrunk fit to couple the suture to the needle.

FIG. 13 is an enlarged, cross-sectional view of the needle-suture combination, taken along line 13—13 of FIG. 12.

DETAILED DESCRIPTION OF THE PREFERRED EMBODIMENTS

The description herein presented refers to the accompanying drawings in which like reference numerals refer to like parts throughout the several views. Referring to FIG. 1, in accordance with the principles of the present invention, there is illustrated a schematic representation of needle-suture combination 10 wherein needle 12 and suture 14 are coupled in coupling area 16.

Turning next to FIG. 2, there is shown an enlarged, exploded view of area 16 depicting the components of the coupling area before the components are coupled. Illustrated are end portion of needle 12 having hub 18 and flange 20, end of suture 14, and heat shrinkable sleeve 22. Hub 18 may include one or more flanges 20 along its length. Either alternately or additionally, hub 18 may include at least one groove 21 disposed peripherally along its length. Preferably, groove 21 is disposed transversely as shown. However, the groove may be longitudinally disposed, if desired, with the groove assuming either a substantially straight or a spiral pathway. Although hub 18 is shown of reduced diameter, which is preferred, it should be understood that the diameter could approximate the diameter of the main body of needle 12. Although not shown, hub 18 could include a groove peripherially located along its length. The groove may be longitudinal but preferably it is circumferentially disposed. Sleeve 22 should be of a body compatible material which may be selected from, but not limited to, a number of heat shrinkable polymers such as a polyolefin, polyethylene and ethyl vinyl acetate, or ethyl vinyl acetate, to name but a few. Sleeve 22 might further include an adhesive 24 located within the sleeve (FIG. 5) but adhesive could be placed along any portion of the length enclosed by the sleeve in use, that is, adhesive could be placed along either hub 18 or suture 14 or both. Any number of adhesive materials would be acceptable, such as, for example, a synthetic polymer classified as a polyolefin.

Now turning to FIG. 3, the components of FIG. 2 are shown positioned for assemblage. Hub 18 and suture 14 are positioned within sleeve 22. Here the end of hub 18 and the end of suture 14 are shown approximated but the ends may be contiguous. The end of suture 14 is preferably stiffened by means of a coating such as nylon or polyester or comparable coating for ease of insertion into sleeve 22. Sleeve 22 has not yet been shrunk fit around hub 18 and suture 14. FIG. 4 depicts that components of FIG. 3 but further illustrates the application of heat to sleeve 22 which causes the sleeve to shrink to tightly surround and secure therewithin hub 18 and the end of suture 14.

Sleeve 22 is initially extruded with a generally uniform wall diameter, internal diameter, and external diameter. The sleeve is then irradiated at a predetermined diameter and memory is set. Thereafter the sleeve is heated to glass transition temperature and expanded with air pressure to a second diameter and then cooled to maintain the expanded diameter. Sleeve 22 is now ready for use in coupling needle 12 and suture 14.

Needle-suture combination 10 includes hardened unannealed or uniformly annealed needle 12 with a small pin-like extension or hub 18 protruding from the back end of the needle. The needle has been hardened in a conventional manner, for example, by heating in a vacuum furnace at 980°–1040° C. followed by tempering at about 260° C. to remove brittleness. The needle can then be attached to suture 14 without annealing (or if working with a very hard needle, with a substantially reduced number of annealings) and without compromising the structural integrity of the needle as a whole. With the needle hub 18 and the suture 14 positioned inside opposite ends of sleeve 22, coupling area 16 is subjected to heat for approximately thirty minutes at a predetermined temperature. The temperature will be in a range of approximately 100°–160° C. for a polyolefin sleeve. The heat shrink temperature, however, will vary depending upon the sleeve material used. The application of heat will cause pre-treated sleeve 22 to shrink and lock hub 18 of needle 12 and the end of suture 14 in position, forming a suture to needle attachment on a non annealed needle or on a uniformly annealed needle.

In the present invention, since there is no annealing, there is no drift of heat down the shank to cause an annealing effect on the shank of the needle. The needle is now uniformly hard along its length and it is possible to place the needle holder at any position along the length of the needle. The resistance to bending is now as high as possible since the needle is as hard as possible, without brittleness. This is in contrast with annealed needles wherein the surgeon had to be careful in the placement of the needle holder on the needle to be sure that he did not grasp a spot which had become soft from the annealing. Also, the ability of the needle to resist rust (the stainlessness) is maintained and the tendency for burr formation at the chop off is greatly decreased or eliminated.

By way of example and not of limitation, polyolefin sleeve 22 having an extruded inside diameter of 0.025 centimeters is irradiated to set the memory at 0.025 centimeters inside diameter. The sleeve is then heated and expanded to 0.050 centimeters inside diameter and cooled to maintain the 0.050 centimeters inside diameter. Needle 12 having hub 18 with a 0.030 centimeters diameter is placed in one end of sleeve 22 and the end of suture 14 having a 0.036 centimeter diameter is placed into the opposite end of sleeve 22. Sleeve 22 with enclosed hub and suture end is then heated at 155° C. for thirty minutes. The sleeve permanently shrinks toward its primary memory setting diameter, locking the needle hub and suture end, securely attaching the needle and suture. In this example, the finished inside diameter of the sleeve over the hub would be 0.030 centimeters and over the suture approximately 0.025 centimeters.

Returning now to the figures, FIG. 6 illustrates a linked, tandem needle-suture combination 100. The connection of needle 12 with hub 18 to suture 15 by means of sleeve 22 is the same as heretofore presented in respect to FIGS. 1–4. Here, however, a second end of suture 15 is connected to an end of another suture 26 by means of sleeve 22 following the same technique as above for the needle to suture coupling. Combination 100 might be useful, for example, when a needle has a first diameter connected to a suture of a lesser diameter followed by a suture having a diameter greater than the diameter of the needle. In this instance, the trailing suture will fully fill a tissue hole made by the needle during use. Typically, the smaller diameter suture will be the weak link in the combination to allow a surgeon to remove the needle from the suture with a sharp snap after the needle has passed through tissue.

FIG. 7 presents alternate embodiment 10' of the needle-suture combination depicted in FIG. 4 and FIG. 8 presents alternate embodiment 100' of the tandem needle-suture combination of FIG. 6. In FIG. 7, sleeve 22 is first heated to shrink to its set memory diameter to capture end of suture 14 at one end of the sleeve while the other end of the sleeve collapses to its shrink diameter. The non suture containing end of sleeve 22 is then placed into a recess in needle 12' for connection thereto by any number of convenient means, such as, gluing, swaging or crimping, to name but a few. In FIG. 8, suture 28 is connected to needle 12' in much the same manner as sleeve 22 of FIG. 7. The end of suture 28 can be placed in a recess in needle 12' for containment therein, for example, by friction fitting, gluing, swaging or crimping. The other end of suture 28 can be coupled to suture 26 by means of shrink sleeve 22 as heretofore disclosed.

Turning next to FIGS. 9–13, there is depicted yet another means for providing a needle-suture combination which has here been designated 10''. Here, needle 12 has hub 30 including groove 32 which accommodates the end portion of suture 14. It should be understood that, if desired, the groove could follow a spiral pathway about the hub and the suture end portion could be placed in the groove so disposed. Sleeve 22 surrounds the end of suture 14 placed in groove 32 of hub 30 (FIG. 11) and, upon application of heat, sleeve 22 shrinks to secure therewithin the end portion of suture 14 and hub 30 for coupling together the needle and the suture. Although not here specifically illustrated, hub 30 could be a full section without groove 32 and the end portion of suture 14 could be juxtaposed with the hub, and sleeve 22 could be shrunk to capture the juxtaposed suture and hub.

Previously, in respect to FIGS. 6 and 8, there was mention of detaching the needle from the suture. This can be accomplished by providing a linking means interposed between and coupling a suture and a needle. The linking means can be a suture having a tensile breaking strength less than the tensile breaking strength of the main suture. Upon application of a tensile axial force, such as that easily applied by a surgeon, along the linking suture of a magnitude sufficient enough to break the linking suture, but less than that force required to break the main suture, the needle can become detached from the suture. In this disclosure, suture 15 in FIG. 6 and suture 28 in FIG. 8 can serve as the linking sutures having an axial tensile rupture strength less than that of suture 26.

In a typical example, a 2-0 intestinal needle is attached to a 2-0 suture having a knot break strength in excess of 2.72 kg. Interposed between the needle and the suture is an 7-0 suture having a 0.25 kg straight break strength. With the coupling of needle and suture as herein presented in respect to either of the embodiments of FIGS. 6 and 8, the assembly is held with the needle in one hand and the 2-0 suture in the other hand. The assembly is then snapped or pulled and the size 7-0 suture which forms the linking means breaks at 0.25 kg. One section of the broken 7-0 suture will remain firmly attached to the needle and the other section will remain firmly attached to the 2-0 suture. Each needle-suture combination so constructed will break at 0.25 kg along the 7-0 weak link section between the needle and the 2-0 suture giving substantially reproducible results.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to an advantage without corresponding use of the other features.

I claim:

1. A needle-suture combination comprising a needle having first and second ends, a suture, and a heat shrunk polymeric sleeve surrounding and anchoring therewithin a first end of said needle and an end of said suture establishing a high strength mechanical attachment between said needle and said suture.

2. A needle-suture combination comprising a needle having first and second ends with one of said ends comprising a hub, a suture positioned substantially coaxially with and having an end disposed face to face with said hub, and a heat shrunk polymeric sleeve (1) surrounding and anchoring therewithin at least a portion of said hub and (2) surrounding and anchoring therewithin said end of said suture, establishing a high strength mechanical attachment coupling together said needle and said suture.

3. The combination according to claim 2 wherein said hub and said end of said suture are proximately disposed.

4. The combination according to claim 2 further including adhesive means disposed along at least a portion of a length surrounded by said sleeve.

5. The combination according to claim 2 further including means for stiffening said end of said suture.

6. The combination according to claim 5 wherein said stiffening means comprises a coating selected from the group consisting of nylon and polyester.

7. A needle-suture combination comprising a needle having first and second ends with one of said ends comprising a hub including at least one groove peripherally disposed about said hub, a suture positioned substantially coaxially with and having an end disposed face to face with said hub, and a heat shrunk polymeric sleeve (1) surrounding and anchoring therewithin at least a portion of said hub and (2) surrounding and anchoring therewithin said end of said suture, establishing a high strength mechanical attachment coupling together said needle and said suture.

8. A needle-suture combination comprising a needle having first and second ends with one of said ends comprising a hub including at least one flange, a suture positioned substantially coaxially with and having an end disposed face to face with said hub, and a heat shrunk polymeric sleeve (1) surrounding and anchoring therewithin at least a portion of said hub and (2) surrounding and anchoring therewithin said end of said suture, establishing a high strength mechanical attachment coupling together said needle and said suture.

* * * * *